(12) United States Patent
Kim et al.

(10) Patent No.: US 11,365,213 B2
(45) Date of Patent: Jun. 21, 2022

(54) COMPOSITION FOR CLEARING SPHEROIDS, METHOD FOR CLEARING SPHEROIDS USING SAME, AND KIT COMPRISING SAME

(71) Applicant: KOREA RESEARCH INSTITUTE OF CHEMICAL TECHNOLOGY, Daejeon (KR)

(72) Inventors: Ki-Suk Kim, Daejeon (KR); Sun Hyun Park, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 16/967,095

(22) PCT Filed: Feb. 1, 2019

(86) PCT No.: PCT/KR2019/001484
§ 371 (c)(1),
(2) Date: Aug. 3, 2020

(87) PCT Pub. No.: WO2019/151838
PCT Pub. Date: Aug. 8, 2019

(65) Prior Publication Data
US 2021/0040139 A1 Feb. 11, 2021

(30) Foreign Application Priority Data
Feb. 5, 2018 (KR) .......... 10-2018-0013747

(51) Int. Cl.
*G01N 1/00* (2006.01)
*C07J 41/00* (2006.01)
*G01N 1/30* (2006.01)

(52) U.S. Cl.
CPC .......... *C07J 41/0066* (2013.01); *G01N 1/30* (2013.01); *G01N 2001/305* (2013.01)

(58) Field of Classification Search
None
See application file for complete search history.

(56) References Cited

U.S. PATENT DOCUMENTS

| 5,413,938 A | * | 5/1995 | Tsujino | .......... G01N 15/12 436/63 |
| 2014/0087419 A1 | | 3/2014 | Miyawaki et al. | |

(Continued)

FOREIGN PATENT DOCUMENTS

| JP | 2003-066035 | 3/2003 |
| JP | 2013-522590 A | 6/2013 |

(Continued)

OTHER PUBLICATIONS

Chung et al., "Structural and Molecular Interrogation of Intact Biological Systems," *Nature* 497: 332-337, May 2013.

(Continued)

*Primary Examiner* — Jyoti Nagpaul
(74) *Attorney, Agent, or Firm* — Klarquist Sparkman, LLP

(57) ABSTRACT

Disclosed are a composition for clearing spheroids, a method for clearing spheroids using same, and a kit comprising same. The composition for clearing spheroids can clear the spheroids in a convenient and rapid manner and thus may be usefully used for imaging of spheroids and in identifying the causes of various diseases, treating the diseases, and predicting the therapeutic effects and toxicity of drugs. In addition, the composition may be used in combination with various medical devices, and in particular, can be prepared as a kit and usefully used as an in vitro medical diagnostic device.

16 Claims, 4 Drawing Sheets

(56) References Cited

U.S. PATENT DOCUMENTS

| | | |
|---|---|---|
| 2015/0285718 A1 | 10/2015 | Hatta et al. |
| 2016/0011086 A1 | 1/2016 | Onodera |
| 2016/0266016 A1 | 9/2016 | Susaki et al. |

FOREIGN PATENT DOCUMENTS

| | | |
|---|---|---|
| JP | 2015-049101 | 3/2015 |
| KR | 10-0287583 | 1/2001 |
| WO | WO 2011/111876 A1 | 9/2011 |
| WO | WO 2012/147965 | 11/2012 |
| WO | WO 2014/069519 | 5/2014 |
| WO | WO 2014/115206 A1 | 7/2014 |
| WO | WO 2015/030164 A1 | 3/2015 |
| WO | WO 2016/108359 | 7/2016 |
| WO | WO 2015/022883 A1 | 3/2017 |
| WO | WO 2017/090777 A1 | 6/2017 |

OTHER PUBLICATIONS

International Search Report from parent PCT Application No. PCT/KR2019/001484, 5 pages (dated May 28, 2019).
Lee et al., "Improved Application of the Electrophoretic Tissue Clearing Technology, CLARITY, to Intact Solid Organs including Brain, Pancreas, Liver, Kidney, Lung, and Intestine," *BMC Developmental Biology* 14: 1-7, Dec. 2014.

* cited by examiner

2)Light sheet confocal microscope

SPECIFICATION

| Area of wells | 29x29mm |
|---|---|
| Well size | 300μm(I.D.) x 300μm(Depth)<br>500μm(I.D.) x 300μm(Depth) |
| Color | Clear |
| No.of wells | 361 micro-wells |
| Model | ISF-361-3(I.D. 300μm well)<br>ISF-361-5(I.D. 500μm well) |
| Material | PDMS(Polydimethylsiloxane) |

COMPOSITION FOR CLEARING SPHEROIDS, METHOD FOR CLEARING SPHEROIDS USING SAME, AND KIT COMPRISING SAME

CROSS-REFERENCE TO RELATED APPLICATIONS

This is the U.S. National Stage of International Application No. PCT/KR2019/001484, filed Feb. 1, 2019, which in turn claims the benefit of priority under 35 U.S.C. § 119 from Korean Patent Application No. 10-2018-0013747, filed on Feb. 5, 2018, the contents of which are incorporated herein by reference in their entirety.

1. Field of the Invention

The present invention relates to a composition for clearing spheroid, a clarity method for spheroid using the same and a kit having the same.

2. Description of the Related Art

Medical diagnostic technology using x-ray has been developed as a technology capable of three-dimensional observation and elaborate diagnosis by two-dimensional scanning such as CT or MRI. Another technique to realize a three dimensional image using ultrasound instead of a light source is also actively used for diagnosis. However, most techniques developed so far have the macro-resolution of millimeter level. The three-dimensional measurement techniques at micro-level that can realize the analysis at cellular level have not been fully established. Thus, moat of cell analysis methods use the conventional two dimensional techniques. That is, in order to analyze the microstructure, a biotissue such as a biopsy tissue or an autopsy tissue is fixed in a fixing solution, and embedded in paraffin or polymer; the sample is made into sections in the thickness of micrometers or nanometers so as to let light or electronic wave pass through; and then transmission Images are observed by optical or electron microscope. To obtain a three dimensional image using the micro-imaging technique, a confocal microscope is needed. With this, thickness information of tens of micrometers can be obtained.

Conventional tissue clearing techniques include Spatleholz, BABB, Scale S, and iDISCO methods, which are the processes of tissue clarification using an organic solvent, and ACT (active CLARITY technology) method, which is a polymer injection method. And the antigen conservative property of the tissues treated by the above methods has been reported. When treated with the methods other than ACT, there is a problem that the conservative property of fluorescence and antigen is reduced. In the case of ACT, it showed more than 90% antigen conservativeness, which shows a higher conservative property compared to a method requiring binding to a hydrogel polymer in addition to a fixed protein such as CLARITY. However, a strong tissue fixation process causes loss of antigenicity, and problems such as reduced antibodies available should be considered. Therefore, various technical improvements are needed.

As for the conventional tissue clarity techniques, Spatleholz, BABB, Scale S, and iDISCO using an organic solvent, and ACT (active clarity technology) using a polymer to maintain the antigen conservation in the treated tissue have been reported. Except ACT, all other methods display the decrease of fluorescence and antigen conservation. In the case of ACT, the antigen conservation reaches at least 90%, which is much higher than other methods using a hydrogel polymer binding to the fixed protein. However, such a strong tissue binding process can cause the loss of antigenicity, resulting in the decrease of valuable antibodies. Therefore, the conventional methods need to be improved.

The 'CLARITY' based technique which was developed recently for tissue clarity, uses a net supporter which is constructed in a tissue to hold materials important for diagnosis such as DNA or proteins by using hydrogel and eliminates lipids selectively (see patent reference 1, and non-patent references 1 and 2).

However, according to the 'CLARITY' based technique above, the hydrogel supporter invades into a tissue. When the concentration of hydrogel is increased, the binding with a protein is increased and the net structure gets tighter, meaning the tissue becomes harder. Once the tissue gets harder, it is hard for the lipid to escape by using a surfactant, indicating time for the clarity process takes longer. In addition, when a CLARITY-specific electrophoresis device is used to rapidly remove lipids, strong voltages or currents pass through the solution and the surface of the tissue and combine with oxygen and the tissue, which causes dark particle deposition or makes the tissue yellow. In particular, the size of spheroids and organoids, not tissues, ranges from hundreds of micro to millimeters, but they are connected by intercellular bonds, causing the sample to be weak, so damage is caused by strong electricity or voltage and hydrolysis by electricity.

In order to acquire a spheroid image, a confocal microscope or the like must be used, and in this case, information of tens of micrometer thickness can be generally obtained. Roughly this thickness is limited by the depth through which the light source can penetrate. However, since the spheroid structures have a size of several hundred micrometers or more, only some information can be obtained in this way. Therefore, in order to obtain information in the thicker tissues, a series of processes of preparing tens of micro-thick successive sections, imaging them through a microscope, and reconstructing them are required. However, since the spheroid sample is fragile, various problems can occur exponentially during the processes of cutting and pasting.

The tissue clearing technology can identify the internal structure and protein distribution of tissues without damaging the tissues, allowing for deeper observation of the tissue structure beyond the observation limits of the existing technology, and access to the integrated structure and molecular information from various systems. Thus, a technology for making the tissue transparent has recently been developed in various ways. However, there is no clearing kit that applies only to the spheroid tissue.

PRIOR ART REFERENCE

Patent Reference (Patent Reference 1) Korean Patent Publication No. WO 2016/108359

Non-Patent Reference (Non-Patent Reference 1) Chung K, et al. (2013) Nature 497(7449):332-337.
(Non-Patent Reference 2) Lee H, et al. BMC Developmental Biology 2014 14:781.

SUMMARY OF THE INVENTION

It is an object of the present invention to provide a composition for clearing spheroid.

It is another object of the present invention to provide a clarity method for spheroid.

It is another object of the present invention to provide a kit for clearing spheroid.

To achieve the above objects, the present invention provides a composition for clearing spheroid comprising a compound represented by formula 1 below, an optical isomer thereof, a hydrate thereof, or a salt thereof:

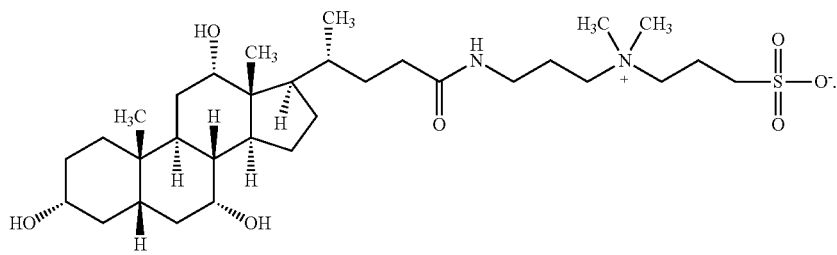

[Formula 1]

In another aspect of the present invention, the present invention provides a method for clearing spheroid comprising a step of clearing the immobilized spheroid by contacting it with the composition.

In another aspect of the present invention, the present invention provides a clarity method for spheroid comprising the following steps:

pretreating a solution containing saccharide to the immobilized spheroid (step 1); and clearing the spheroid pretreated in step 1 by contacting it with the composition (step 2).

In another aspect of the present invention, the present invention provides a kit for clearing spheroid comprising a spheroid clearing pretreatment composition containing a saccharide solution; and the composition for clearing spheroid of claim 1.

Advantageous Effect

A composition for clearing spheroid comprising a compound of formula 1 can clear spheroid conveniently and quickly, so it can be useful for imaging spheroid, and can be effectively used for identifying the causes of various diseases, treating them, and predicting the effectiveness and toxicity of drugs. In addition, the composition can be used by applying to various medical devices, and in particular, it can be used as an in vitro diagnostic device by making it as a kit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Left: a graph showing the change in the number of cells in the spheroid before and after clarification analyzed with a JuLI live cell movie analyzer, and Right: images showing the fluorescence brightness of the spheroid before and after clarification analyzed with a general microscope.

Figure 3:
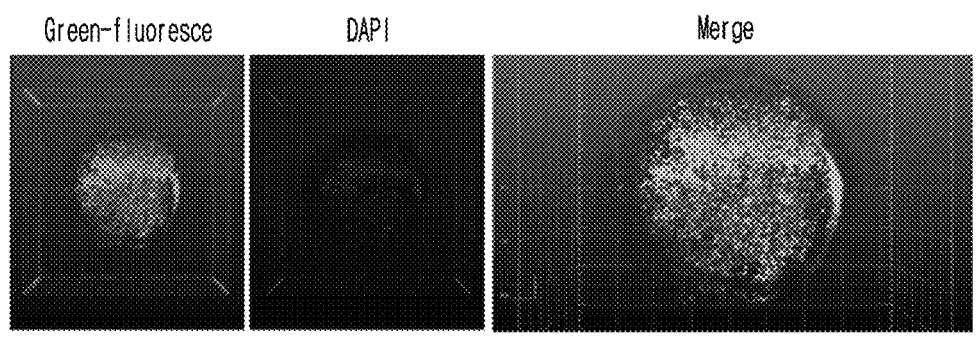

FIG. 3 shows the fluorescence brightness of the spheroid after clarification measured using a microscope.

Figure 4:
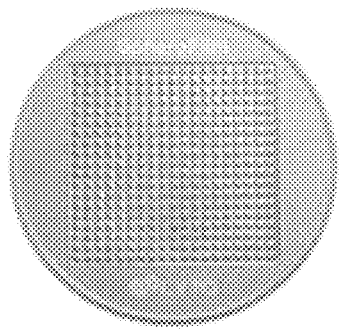

FIG. 4 shows the information of the SpheroidFilm used in the experimental examples of the present invention.

DESCRIPTION OF THE PREFERRED EMBODIMENTS

As shown in FIG. 3, it can be seen that the resolution of the shape of each cell and the shape of the nucleus can be clearly confirmed in three dimensions.

Hereinafter, the present invention is described in detail.

The present invention provides a composition for clearing spheroid comprising a compound represented by formula 1 below, an optical isomer thereof, a hydrate thereof, or a salt thereof:

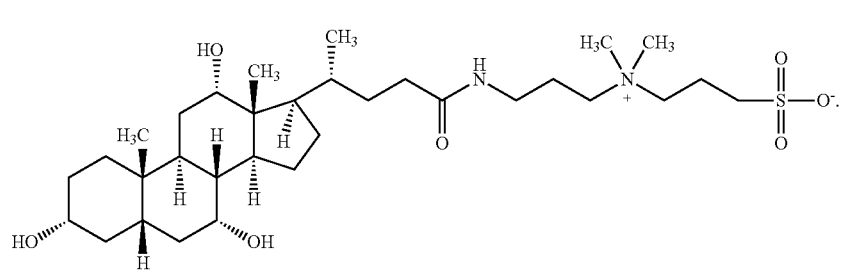

[Formula 1]

Hereinafter, the composition for clearing spheroid is described in detail.

The compound represented by formula 1 can be a compound represented by formula A below.

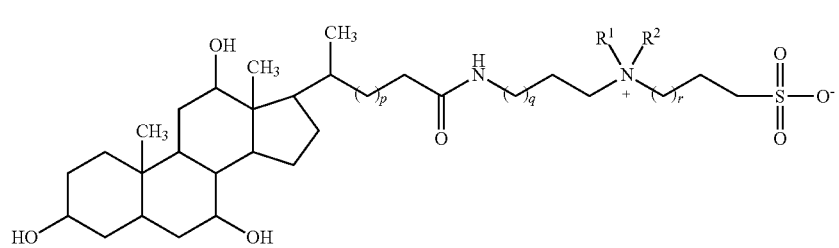

[Formula A]

In the formula A, $R^1$ and $R^2$ are independently $C_{1-10}$ straight or branched alkyl; and p, q and r are independently integers of 0~10.

$R^1$ and $R^2$ are independently $C_{1-5}$ straight or branched alky; and p, q and r are independently integers of 0~5.

$R^1$ and $R^2$ are methyl; and p, q and r are the integer 1.

The composition for clearing spheroid of the present invention removes the lipid components that block the penetration of light and other molecules from the spheroid, does not cause structural denaturation of proteins, and hardens the tissue.

In the composition for clearing spheroid, the concentration of the compound represented by formula 1 can be included in the concentration of 2-55 w/v % (weight/volume %), and can be used in the concentration of 40 w/v % for the application to a sample. At this time, the solution for indicating the concentration can be the generally used simulated body fluid, more particularly, distilled water, PBS (phosphate buffer saline), TBS (tris buffer solution), etc., but not always limited thereto.

When the concentration of the compound represented by formula 1 is included less than 2 w/v %, the clearing rate of spheroid may be remarkably slowed, and when the concentration of the compound represented by formula 1 is included more than 60 w/v %, the compound represented by formula 1 may not be dissolved completely.

The composition for clearing spheroid can further include a material that controls the osmotic pressure to accelerate the spheroid clarification. At this time, as the material for rapidly accelerating the spheroid clarification, urea, CHAPSO (3-([3-Cholamidopropyl] dimethylammonio)-2-hydroxy-1-propanesulfonate), sucrose, fructose (fructose), glycerol, diatrizoic acid, Triton X-100, Tween-20, 2,2'-thioethanol, iohexol, chloral hydrate, or a combination thereof can be used, but not always limited thereto.

The material for rapidly accelerating the spheroid clarification can be included at the concentration of 5~80 w/v %, 5~75 w/v %, 10~70 w/v %, 5~50 w/v %, or 35~60 w/v %. At this time, when the concentration is less than 5 w/v %, the rate of clearing the tissue is slowed, and when the concentration is more than 80 w/v %, crystals can be formed or cannot be dissolved in the solution. In one specific example, if urea is used as the material for rapidly accelerating the spheroid clarification, the concentration of urea can be 10~70 w/v %, and preferably 20~60 w/v %. In addition, the concentration of the material for rapidly accelerating the spheroid clarification can be appropriately adjusted with the preferred concentration range of the compound represented by formula 1.

The said spheroid can be prepared using the cells derived from the tissues separated from the living body, specifically brain, blood vessel, liver, lung, kidney, pancreas, heart, and intestines, but not always limited thereto.

That is, the composition for clearing spheroid of the present invention can be applied to the spheroid made of various cells, in particular, the spheroid and organoid prepared using the cells derived from brain, blood vessel, liver, lung, kidney, pancreas, intestine, heart, etc. The clearing can occur in whole or in part of the spheroid or organoid.

After the spheroid was clarified by using the composition for clearing spheroid, before and after clarification were compared. After being clarified, the number of recognized cells was significantly increased, the brightness of the fluorescence was significantly increased, and the resolution of the shape of each cell and the shape of the nucleus was clearly confirmed in three dimensions (see Experimental Example 2 and FIGS. 2 and 3).

The composition for clearing spheroid does not require expensive electrophoresis devices and expensive solutions, and improves spheroid transparency without tissue swelling, bubble formation, discoloration, and black sediment.

The composition for clearing spheroid can clear spheroid conveniently and quickly, so it can be useful for imaging spheroid, and can be effectively used for identifying the causes of various diseases, treating them, and predicting the effectiveness and toxicity of drugs. In addition, the composition can be used by applying to various medical devices, and in particular, it can be used as an in vitro diagnostic device by making it as a kit.

In addition, by using the above composition, it is possible to conveniently prepare and clarify spheroid at the same time, and through this, the three-dimensional distribution of cells and molecules can be imaged and observed. Therefore, observational studies can be performed with a size of several hundred micrometers or more in one complete structure for various spheroids having complex structures. So, the composition can be effectively used to identify the causes of various diseases and to predict the treatment method, and further, the effectiveness and toxicity of drugs.

In another aspect of the present invention, the present invention provides a clarity method for spheroid comprising a step of clearing the immobilized spheroid by contacting it with the composition for clearing spheroid.

The clarity method for spheroid includes a step of clearing the immobilized spheroid by contacting it with the composition for clearing spheroid.

Particularly, in the clarity method for spheroid according to the present invention, the physicochemical properties of the spheroid are modified and made transparent to make light penetrate deeper and make it transparent by contacting the immobilized spheroid with a composition containing the compound represented by formula 1.

The clarity method for spheroid according to the present invention improves spheroid transparency without bubble formation, discoloration, and black sediment, and does not lose or distort information in a desired tissue due to protein denaturation or the like. Therefore, various fluorophores such as GFP protein can be used to detect information in the tissues.

In the clarity method for spheroid according to the present invention, the spheroid can be immobilized without any particular limitation, as long as it is a method of immobilizing the spheroid without causing loss of antigenicity prior to clarification.

More particularly, the immobilization of the spheroid can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide or a combination thereof, but not always limited thereto.

In the clarity method for spheroid according to the present invention, when a mixture of the compound represented by formula 1 and urea is treated, the structural binding force of the protein is increased, denaturation does not occur, the tissue is hardened, the swelling that appears in the spheroid clearing process is prevented, and the cracking of the tissue occurring in the processes of antibody treatment and washing can be prevented. At this time, the solution for indicating the concentration can be the generally used simulated body fluid, more particularly, distilled water, PBS (phosphate buffer saline), TBS (tris buffer solution), etc., but not always limited thereto. The reaction can be performed in a temperature range of 10° C.~50° C., 12° C.~48° C., 14° C.~46° C., 16° C.~44° C., 18° C.~42° C., 20° C.~40° C., 24° C.~39° C., 28° C.~38° C., 30° C.~37° C., and 33° C.~34° C.

In the composition for clearing spheroid, the concentration of the compound represented by formula 1 can be included in the concentration of 2-55 w/v % (weight/volume %), and can be used in the concentration of 40 w/v % for the application to a sample. At this time, the solution for indicating the concentration can be the generally used simulated body fluid, more particularly, distilled water, PBS (phosphate buffer saline), TBS (tris buffer solution), etc., but not always limited thereto.

When the concentration of the compound represented by formula 1 is included less than 2 w/v %, the clearing rate of spheroid may be remarkably slowed, and when the concentration of the compound represented by formula 1 is included more than 60 w/v %, the compound represented by formula 1 may not be dissolved completely.

The said spheroid can be prepared using the cells derived from the tissues separated from the living body, specifically brain, blood vessel, liver, lung, kidney, pancreas, heart, and intestines, but not always limited thereto.

The method can be conducted in a temperature range of 4° C.~50° C.

The composition for clearing spheroid of the present invention can include the compound represented by formula 1 or the hydrate thereof at the concentration of 2~55 w/v % (weight/volume %), and preferably at the concentration of 4~50 w/v %. At this time, the solution for indicating the concentration can be the generally used simulated body fluid, more particularly, distilled water, PBS (phosphate buffer saline), TBS (tris buffer solution), etc., but not always limited thereto. When the concentration of the compound represented by formula 1 is included less than 2 w/v %, the clearing rate of spheroid may be remarkably slowed, and when the concentration of the compound represented by formula 1 is included more than 55 w/v %, the compound represented by formula 1 may not be dissolved in the composition for clearing spheroid completely.

The composition for clearing spheroid can further include a material that controls the osmotic pressure to accelerate the spheroid clarification. At this time, as the material for rapidly accelerating the spheroid clarification, urea, CHAPSO (3-([3-Cholamidopropyl] dimethylammonio)-2-hydroxy-1-propanesulfonate), sucrose, fructose (fructose), glycerol, diatrizoic acid, Triton X-100, Tween-20, 2,2'-thioethanol, iohexol, chloral hydrate, or a combination thereof can be used, but not always limited thereto.

The material for rapidly accelerating the spheroid clarification can be included at the concentration of 5~80 w/v %, 5~75 w/v %, 10~70 w/v %, 5~50 w/v %, or 35~60 w/v %. At this time, when the concentration is less than 5 w/v %, the rate of clearing the tissue is slowed, and when the concentration is more than 80 w/v %, crystals can be formed or cannot be dissolved in the solution. In one specific example, if urea is used as the material for rapidly accelerating the spheroid clarification, the concentration of urea can be 10~70 w/v %, and preferably 20~60 w/v %. In addition, the concentration of the material for rapidly accelerating the spheroid clarification can be appropriately adjusted with the preferred concentration range of the compound represented by formula 1.

In another aspect of the present invention, the present invention provides a clarity method for spheroid comprising the following steps: pretreating a solution containing saccharide to the immobilized spheroid (step 1); and clearing the spheroid pretreated in step 1 by contacting it with the composition for clearing spheroid (step 2).

In the clarity method for spheroid, step 1 is a pretreatment step of treating a solution containing saccharide to the immobilized spheroid.

The said spheroid can be prepared using the cells derived from the tissues separated from the living body, specifically brain, blood vessel, liver, lung, kidney, pancreas, heart, and intestines, but not always limited thereto.

The immobilization of the spheroid can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide or a combination thereof, but not always limited thereto.

The saccharide can be monosaccharide, disaccharide, polysaccharide, etc., and more specifically, the monosaccharide is fructose, galactose, glucose or mannose; the disaccharide is sucrose, lactose, maltose, trehalose, turanose or cellobiose; and the polysaccharide is dextran, diethylamino ethyl-dextran, dextrin, cellulose or β-glucan. Preferably, sucrose can be used as the saccharide. In addition, the solution containing saccharide is preferably an aqueous solution containing saccharide.

The saccharide concentration of the solution containing (comprising) saccharide can be in the range of 10~70 w/v %, 20~60 w/v %, 25~50 w/v %, and 30~40 w/v %.

When the saccharide solution is treated to the spheroid, the lipid components that block the penetration of light and other molecules are removed from the spheroid in advance and dehydration is induced, and consequently the structural binding force of the reagent that immobilizes the tissue and the spheroid is increased, which does not cause denaturation. In addition, it is possible to make the tissue harder, to prevent the tissue swelling that appears in the spheroid clearing process, and to prevent the cracking of the tissue occurring in the processes of antibody treatment and washing. However, when the saccharide concentration of the solution containing saccharide is less than 10 w/v %, there is a problem that the effect does not occur, and when the saccharide concentration of the solution containing saccharide is more than 70 w/v %, there is a problem that is not economical.

In the clarity method for spheroid, step 2 is a step of clearing the spheroid pretreated in step 1 by contacting it with a composition for clearing spheroid comprising a CHAPS compound represented by formula 1 or a hydrate thereof.

The step 2 includes a step of clearing the spheroid immobilized and pretreated by contacting it with a composition for clearing spheroid. Particularly, in the clarity method for spheroid according to the present invention, the physicochemical properties of the spheroid are modified and made transparent to make light penetrate deeper and make it transparent by contacting the immobilized spheroid with a composition comprising the compound represented by formula 1.

The clarity method for spheroid according to the present invention improves spheroid transparency without bubble formation, discoloration, and black sediment, and does not lose or distort information in a desired tissue due to protein denaturation or the like. Therefore, various fluorophores such as GFP protein can be used to detect information in the tissues.

In the composition for clearing spheroid, the concentration of the compound represented by formula 1 can be included in the concentration of 2-55 w/v % (weight/volume %), and can be used in the concentration of 40 w/v % for the application to a sample. At this time, the solution for indicating the concentration can be the generally used simulated body fluid, more particularly, distilled water, PBS (phosphate buffer saline), TBS (tris buffer solution), etc., but not always limited thereto.

When the concentration of the compound represented by formula 1 is included less than 2 w/v %, the clearing rate of spheroid may be remarkably slowed, and when the concentration of the compound represented by formula 1 is included more than 60 w/v %, the compound represented by formula 1 may not be dissolved completely.

In the clarity method for spheroid according to the present invention, the spheroid can be immobilized without any particular limitation, as long as it is a method of immobilizing the spheroid without causing loss of antigenicity prior to clarification.

More particularly, the immobilization of the spheroid can be performed by the conventional method using paraformaldehyde, ethylene glycol diglycidyl ether, dipropylene glycol diglycidyl ether, 1,4-butanediol diglycidyl ether, glycerol polyglycidyl ether, glutaraldehyde, polyacrylamide or a combination thereof, but not always limited thereto.

In the clarity method for spheroid according to the present invention, when a mixture of the compound represented by formula 1 and urea is treated, the structural binding force of the protein is increased, denaturation does not occur, the tissue is hardened, the swelling that appears in the spheroid clearing process is prevented, and the cracking of the tissue occurring in the processes of antibody treatment and washing can be prevented. At this time, the solution for indicating the concentration can be the generally used simulated body fluid, more particularly, distilled water, PBS (phosphate buffer saline), TBS (tris buffer solution), etc., but not always limited thereto. The reaction can be performed in a temperature range of 10° C.~50° C., 12° C.~48° C., 14° C.~46° C., 16° C.~44° C., 18° C.~42° C., 20° C.~40° C., 24° C.~39° C., 28° C.~38° C., 30° C.~37° C., and 33° C.~34° C.

The method can be conducted in a temperature range of 4° C.~50° C.

The composition for clearing spheroid can further include a material that controls the osmotic pressure to accelerate the spheroid clarification. At this time, as the material for rapidly accelerating the spheroid clarification, urea, CHAPSO (3-([3-Cholamidopropyl] dimethylammonio)-2-hydroxy-1-propanesulfonate), sucrose, fructose (fructose), glycerol, diatrizoic acid, Triton X-100, Tween-20, 2,2'-thioethanol, iohexol, chloral hydrate, or a combination thereof can be used, but not always limited thereto.

At this time, the material for rapidly accelerating the spheroid clarification can be included at the concentration of 5~80 w/v %, 5~75 w/v %, 10~70 w/v %, 5~50 w/v %, or 35~60 w/v %. At this time, when the concentration is less than 5 w/v %, the rate of clearing the tissue is slowed, and when the concentration is more than 80 w/v %, crystals can be formed or cannot be dissolved in the solution. In one specific example, if urea is used as the material for rapidly accelerating the spheroid clarification, the concentration of urea can be 10~70 w/v %, and preferably 20~60 w/v %. In addition, the concentration of the material for rapidly accelerating the spheroid clarification can be appropriately adjusted with the preferred concentration range of the compound represented by formula 1.

In another aspect of the present invention, the present invention provides a kit for clearing spheroid comprising a spheroid clearing pretreatment composition containing a saccharide solution; and a composition for clearing spheroid of claim 1.

The composition for clearing spheroid comprising the compound represented by formula 1 can clear spheroid conveniently and quickly, so the kit for clearing spheroid comprising the same can be useful for imaging spheroid, and can be effectively used for identifying the causes of various diseases, and predicting the therapeutic effect, effectiveness and toxicity of drugs.

Hereinafter, the present invention will be described in detail by the following examples and experimental examples.

However, the following examples and experimental examples are only for illustrating the present invention, and the contents of the present invention are not limited thereto.

Experimental Example 1

Confirmation of Change in Size of Clarified Tissue

In order to evaluate the ability to clarify the spheroid of the composition for clearing the stem cell aggregate (spheroid) according to the present invention, specifically, to confirm that the clearing is well performed without damaging the spheroid, the following experiment was performed.

All the animal tests described in this statement were performed according to the guidance (Approval No. RS17003) of Committee for Animal Resources, Korea Institute of Toxicology.

Step 1: Formation and Immobilization of Spheroid

First, mother mice were anesthetized with isoflurane (1 cc/min), an inhalation anesthetic, and the hearts of 15 fetuses were extracted. The extracted fetal hearts were placed in 0.2% trypsin solution, followed by chopping. The chopped heart tissues were placed in an enzyme solution and incubated for 20 minutes. The heart cells were well separated and sprayed on the SpheroidFilm. Then, a spheroid was allowed to form in the cell incubator. After formation of the spheroid, molecular probes qtracker 525 labeling kit (Cat #Q25049) for cytoplasm staining and DAPI (sigma Cat #D 9542) for nuclear staining were treated for 2 hours. When the cytoplasm and nucleus were stained, washing was performed with PBS and the spheroid was fixed with paraformaldehyde for 12 hours.

Step 2: Clarification of Spheroid Using Composition

To prevent spheroid damage, SpheroidFilm was added to 1% low melting agarose in a 45° C. aqueous solution. The SpheroidFilm was sufficiently moistened with agarose and then hardened at room temperature. In the case of bubbling, the bubbles were removed using an insulin syringe needle and then the film was hardened at room temperature. The SpheroidFilm fixed with agarose was incubated in a mixed solution containing CHAPS (40 w/v %) and urea (40 w/v %) at 37° C., at 100 rpm for 24~48 hours. The clarified spheroid was washed with distilled water for 4 hours. Finally, the sample was placed in a mounting solution and incubated for 24 hours.

Figure 1:
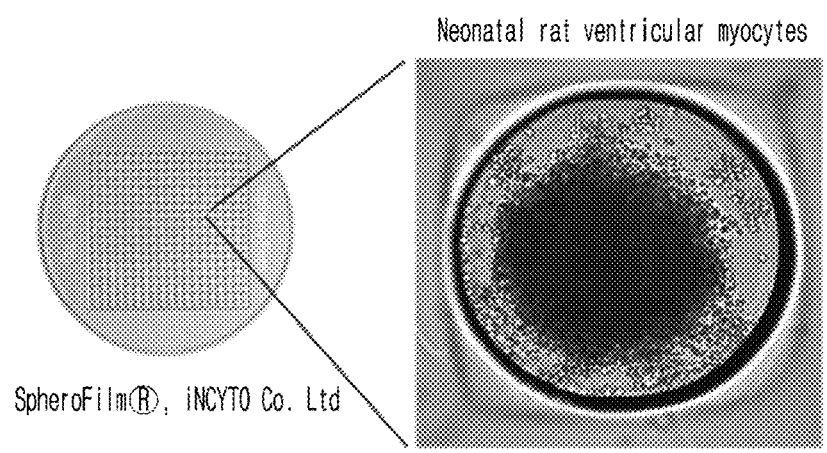
FIG. 1 is a set of images that the spheroid is formed on SpheroidFilm.

FIG. 1 is a set of images that the spheroid is formed on SpheroidFilm.

As shown in FIG. 1, it can be seen that the spheroid was formed normally.

As shown in the above results, it was confirmed that the spheroid could be conveniently prepared and clarified simultaneously by using the composition for clearing spheroid of the present invention.

Experimental Example 2

Analysis of Clarified Spheroid

To confirm the degree of clarification of the spheroid clarified in Experimental Example 1, the number of recognizable cells in the spheroid and the fluorescence brightness before and after clarification were measured.

2-1. Measurement of Number of Recognized Cells in Spheroid Before and After Clarification The changes in the number of cells before and after clarification were observed, and the results were analyzed with a JuLI live cell movie analyzer and shown in FIG. 2.

Figure 2:
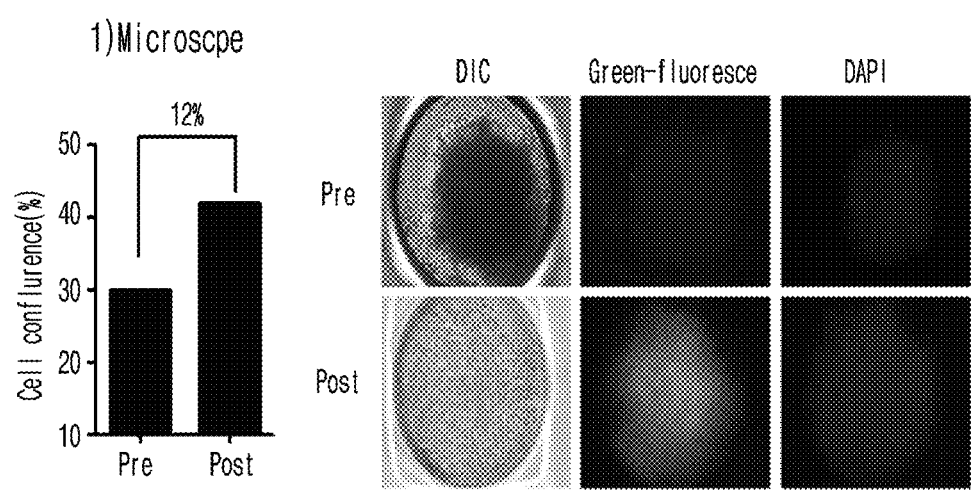
FIG. 2 shows the spheroid analyzed before and after clarification.

The left diagram of FIG. 2 is a graph showing the changes in the number of cells in the spheroid before and after clarification analyzed with a JuLI live cell movie analyzer.

As shown in the left diagram of FIG. 2, about 30% of the cells were recognized before the clarification, while the cells recognized by the JuLi cell analyzer were increased to 42% after the clarification. Once clarified, the cell-like contour appeared, so it was recognized as a cell in the JuLi system. That is, after clarifying the spheroid with the clearing composition of the present invention, the number of recognized cells was significantly increased, this suggests that the clearing composition of the present invention has an excellent effect of clearing the spheroid.

2-2. Measurement of Fluorescence Brightness of Spheroid Before and After Clarification with General Microscope The fluorescence brightness before and after clarification was compared using a general microscope, and the results are shown in FIG. 2. The right diagram of FIG. 2 is a set of images showing the fluorescence brightness of the spheroid before and after clarification analyzed with a general microscope.

As shown in the right diagram of FIG. 2, when comparing the fluorescence brightness before and after clarification using a general microscope, the green-fluoresce fluorescence was hardly observed before clarification, but the fluorescence brightness was significantly increased after clarification. The fluorescence of DAPI was also increased significantly after clarification than before.

In addition, it was visually confirmed from the DIC results that the spheroid was clarified.

2-3. Measurement of Fluorescence Brightness of Spheroid After Clarification with Microscope To obtain three-dimensional bioimages, green fluorescence and DAPI signals were confirmed using 5× objective lens under a macro laser light-sheet illumination imaging system confocal microscope. The results are shown in FIG. 3.

FIG. 3 shows the fluorescence brightness of the spheroid after clarification measured using a microscope.

As shown in FIG. 3, it can be seen that the resolution of the shape of each cell and the shape of the nucleus can be clearly confirmed in three dimensions.

The composition for clearing spheroid comprising the compound of formula 1 of the present invention can clear spheroid conveniently and quickly, so it can be useful for imaging spheroid, and can be effectively used for identifying the causes of various diseases, treating them, and predicting the effectiveness and toxicity of drugs. In addition, the composition can be used by applying to various medical devices, and in particular, it can be used as an in vitro diagnostic device by making it as a kit.

What is claimed is:

1. A composition for clearing of a spheroid comprising 2 to 60 w/v % of a compound represented by formula 1 below, an optical isomer thereof, a hydrate thereof, or a salt thereof; and 20 to 60 w/v % of urea:

[Formula 1]

2. The composition according to claim 1, wherein the composition comprises 40 w/v % of a compound represented by formula 1 below, an optical isomer thereof, a hydrate thereof, or a salt thereof; and 40 w/v % of urea.

3. The composition according to claim 1, wherein the spheroid is prepared using cells derived from brain, blood vessel, liver, lung, kidney, pancreas, heart, or intestines.

4. A method for clearing of a spheroid comprising contacting a fixed spheroid with the composition of claim 1.

5. The method of claim 4, further comprising fixing the spheroid using one or more of paraformaldehyde, ethylene glycol diglycidyl ether, dipropylene glycol diglycidyl ether, 1,4-butanediol diglycidyl ether, glycerol polyglycidyl ether, glutaraldehyde and polyacrylamide.

6. The method of claim 4, wherein the spheroid is prepared using cells derived from brain, blood vessel, liver, lung, kidney, pancreas, heart, or intestines.

7. The method of claim 4, wherein the method is conducted in a temperature range of 4° C.~50° C.

8. A method for clearing of a spheroid comprising the following steps:
   pretreating a fixed spheroid with a solution containing saccharide (step 1); and
   clearing the spheroid pretreated in step 1 by contacting the pretreated spheroid with the composition of claim 1 (step 2).

9. The method of claim 8, further comprising fixing the spheroid using one or more of paraformaldehyde, ethylene glycol diglycidyl ether, dipropylene glycol diglycidyl ether, 1,4-butanediol diglycidyl ether, glycerol polyglycidyl ether, glutaraldehyde and polyacrylamide.

10. The method of claim 8, wherein the spheroid is prepared using cells derived from brain, blood vessel, liver, lung, kidney, pancreas, heart, or intestines.

11. The method of claim 8, wherein the method is conducted in a temperature range of 4° C.~50° C.

12. The method of claim 8, wherein the solution containing saccharide comprises one or more of monosaccharide, disaccharide, and polysaccharide.

13. The method of claim 12, wherein the monosaccharide is fructose, galactose, glucose or mannose; the disaccharide is sucrose, lactose, maltose, trehalose, turanose or cellobiose; and the polysaccharide is dextran, diethylamino ethyldextran, dextrin, cellulose or β-glucan.

14. The method of claim 8, wherein the solution containing saccharide is an aqueous solution containing saccharide.

15. The method of claim 8, wherein the saccharide concentration of the solution containing saccharide is 10~70 w/v %.

16. A kit for clearing of a spheroid comprising a spheroid clearing pretreatment composition containing a saccharide solution; and the composition for clearing spheroid of claim 1.

* * * * *